United States Patent [19]
Colligan

[11] Patent Number: 5,667,528
[45] Date of Patent: Sep. 16, 1997

[54] BRAIDED SUTURE SURGICAL INCISION MEMBER ATTACHMENT

[75] Inventor: Francis D. Colligan, New Haven, Conn.

[73] Assignee: United States Surgical Corporation, Norwalk, Conn.

[21] Appl. No.: 561,646

[22] Filed: Nov. 22, 1995

[51] Int. Cl.⁶ .................................................. A61B 17/06
[52] U.S. Cl. .......................... 606/224; 606/225; 606/226
[58] Field of Search ........................ 606/139, 148, 606/224, 225, 226, 222, 228, 229, 230, 331

[56] References Cited

U.S. PATENT DOCUMENTS

| | | | |
|---|---|---|---|
| 3,918,455 | 11/1975 | Coplan | 128/339 |
| 4,510,934 | 4/1985 | Batra | 128/335.5 |
| 5,007,922 | 4/1991 | Chen et al. | |
| 5,019,093 | 5/1991 | Kaplan et al. | |
| 5,059,213 | 10/1991 | Chesterfield et al. | |
| 5,080,667 | 1/1992 | Chen et al. | |
| 5,181,923 | 1/1993 | Chesterfield et al. | |
| 5,259,845 | 11/1993 | Korthoff. | |
| 5,259,846 | 11/1993 | Granger et al. | |
| 5,261,886 | 11/1993 | Chesterfield et al. | |
| 5,269,783 | 12/1993 | Sander | 606/72 |
| 5,269,808 | 12/1993 | Proto et al. | |
| 5,280,674 | 1/1994 | Granger et al. | |
| 5,306,289 | 4/1994 | Kaplan et al. | |
| 5,318,577 | 6/1994 | Li. | |
| 5,383,902 | 1/1995 | Carpentiere et al. | |
| 5,403,345 | 4/1995 | Spingler. | |
| 5,507,777 | 4/1996 | Kus et al. | 606/224 |

FOREIGN PATENT DOCUMENTS 0647431 4/1995 European Pat. Off.

*Primary Examiner*—Michael Buiz
*Assistant Examiner*—Tina T.D. Pham

[57] ABSTRACT

A method for attaching a multifilament suture having a sheath and core structure to a surgical incision member includes removing a length of core material from an end portion of the suture, and inserting the coreless sheath into the surgical incision member aperture. The coreless sheath of the end portion may optionally be tipped prior to insertion into the surgical incision member.

11 Claims, 3 Drawing Sheets

BRAIDED SUTURE SURGICAL INCISION MEMBER ATTACHMENT

BACKGROUND

1. Technical Field

The method disclosed herein relates to the attachment of a braided suture to a surgical incision member.

2. Background of the Art

Surgical incision members and sutures are long known in the art. Referring to FIG. 1, a prior art surgical incision member-suture combination is shown. The typical surgical incision member 10 comprises a shaft having a pointed tip 11 at one end for piercing tissue, and a barrel portion 12 at the other end. The shaft may be curved, as shown, or straight. An axial bore 13 in the barrel end 12 is provided to receive the end portion of a surgical suture 20.

The suture can be a monofilament or multifilament suture, and can be bioabsorbable or non-bioabsorbable. The suture is generally tipped to create a stiffened non-brooming end which can be inserted into the bore in the surgical incision member. The barrel end of the surgical incision member is then crimped to retain the suture.

To reduce trauma to body tissue, it is desirable to have a surgical incision member of the smallest diameter necessary to perform the intended operation. Ideally, the diameter of the surgical incision member would be no larger than the diameter of the suture. However, surgical incision members are usually larger in diameter than the sutures because the sutures must be accommodated by the surgical incision member bore, which necessarily is smaller than the surgical incision member outer diameter. One way of minimizing the surgical incision member diameter is by allowing a thinner surgical incision member wall diameter around the bore. However, this has the disadvantage of weakening the metal and increasing the possibility that the metal will crack or shatter when the barrel end is crimped.

What is needed, then, is a method for attaching a suture to a surgical incision member which allows use of a thinner surgical incision member, preferably one which is no larger than the suture.

SUMMARY

Provided herein is a method for attaching a multifilament suture having a core and sheath structure to a surgical incision member having an aperture for receiving the suture. The method advantageously permits the attachment of a suture to a surgical incision member no larger in diameter than the suture and comprises removing a length of core material from an end portion of the suture, then inserting the end portion into the surgical incision member aperture. The core can be removed by grasping the sheath and the end of the core, retracting the sheath to expose a length of core material, and cutting and removing the length of core material. The sheath is then advanced to its original position and forms a coreless end portion of the suture which can be inserted into the surgical incision member aperture. Optionally, the coreless end portion can be reduced in diameter by tension and tipped prior to insertion in the surgical incision member.

DETAILED DESCRIPTION OF PREFERRED EMBODIMENTS

The method described herein relates to multifilament sutures having sheath and core structures. Such sutures are disclosed, for example, in U.S. Pat. Nos. 5,019,093, 5,181,923, 5,059,213, 5,261,886, and 5,306,289, all of which are incorporated by reference herein. An advantage to the sheath-core construction is that the sheath and core can optionally be differently fabricated. For example, the core can be twisted or cabled while the sheath can be braided. Also, the core yarns and sheath yarns can be fabricated from different materials and/or from different sized yarns. These factors enable sutures to be made with a wide range of handling characteristics and suturing qualities.

The suture used in the method described herein can be bioabsorbable or non-bioabsorbable, and may contain coating and/or filling materials for lubricity and storage stabilization as well as medically useful treating agents, such as antibiotics, healing agents, tissue growth promoters, and the like. Such materials are described in U.S. Pat. No. 5,059,213, for example.

Suture sizes are expressed in terms of standard sizes corresponding to certain ranges of diameter (in millimeters), as set forth in the United States Pharmacopoeia (USP). Standard sizes of braided sutures are set forth in Table I below:

TABLE I

| SUTURE SIZE | |
|---|---|
| USP Suture Size | Diameter (mm) |
| 2 | 0.50–0.599 |
| 1 | 0.40–0.499 |
| 0 (1/0) | 0.35–0.399 |
| 2/0 | 0.30–0.399 |
| 3/0 | 0.20–0.249 |
| 4/0 | 0.15–0.199 |
| 5/0 | 0.10–0.149 |
| 6/0 | 0.070–0.099 |
| 7/0 | 0.050–0.069 |
| 8/0 | 0.040–0.049 |

Generally, the core diameter of a cored suture is about 50%–70% of the total suture diameter. The method employed herein involves removal of the core from the end portion of the suture, leaving only the sheath.

Figure 2:
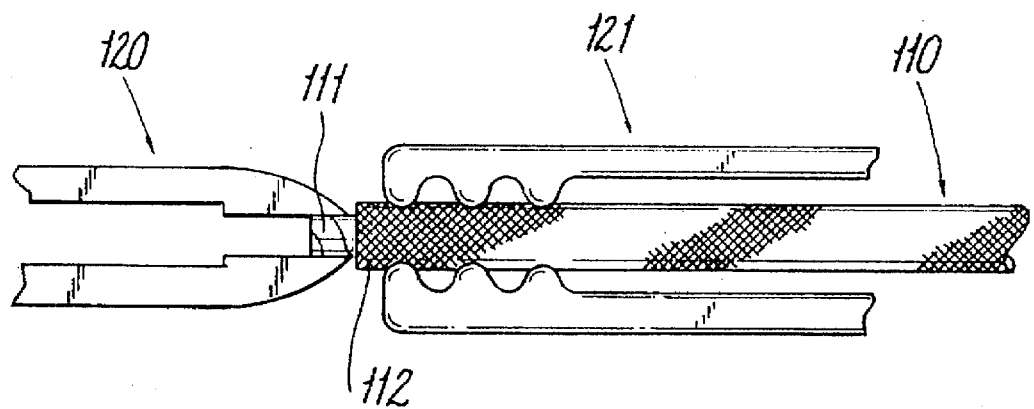
FIGS. 2 to 5 are diagrammatic views illustrating the steps of the method described herein.

Referring to FIG. 2, a suture 110 is grasped along its outer sheath surface by grasper 121. The end portion of the core 111 protrudes beyond the end of the sheath 112 and is grasped by pincers 120. It has been found that when a cored suture is freshly cut, the sheath retracts slightly leaving a tip of the core exposed. This retraction of the sheath can be enhanced by cutting the suture while the suture is under tension. The sheath will retract further as it returns to a more relaxed configuration.

Figure 3:
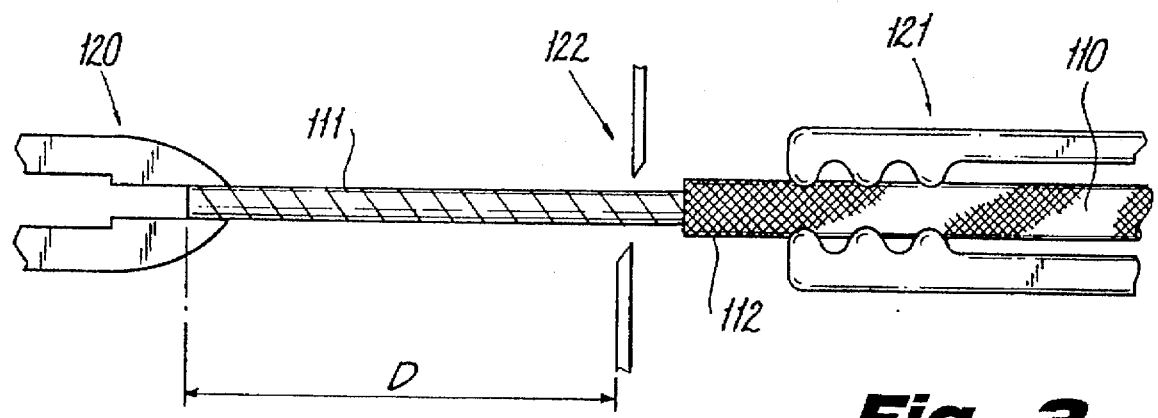

Referring now to FIG. 3, the grasper 121 is used to proximally pull the sheath 112 backwards leaving an exposed end portion of core 111. The suture 110 is secured at a position (not shown) proximal to the position where graspers 121 grip the sheath 112. Thus, the sheath strands bunch up behind the grasper 121.

A cutter 122, which is shown as a pair of opposing sharp edged blades, is used to slice the core strands 111 at a spaced apart position held by pincers 120. Generally, the distance D, which is the length of core 111 removed by this procedure, is at least equal to the depth of the surgical incision member bore into which the suture will be inserted, and preferably ranges from 0.1 inch to 2 inches. Alternatively, longer lengths of core 111 can be removed to accommodate the surgical application in which the suture is intended to be used.

After the core 111 is cut and removed, the grasper 121 moves the sheath 112 distally forward and pincers 120 grasp the end of the sheath 112. Grasper 121 is then disengaged from the suture, moved rearward and reengaged with the suture to secure the suture 110 at a proximal position. Tension is then applied to the suture 110 by biasing pincers 120 and grasper 121 in opposite directions. This tension causes the suture strands to tighten and close up the interstitial spaces between the filaments, thereby minimizing the overall diameter of the suture.

Figure 4:
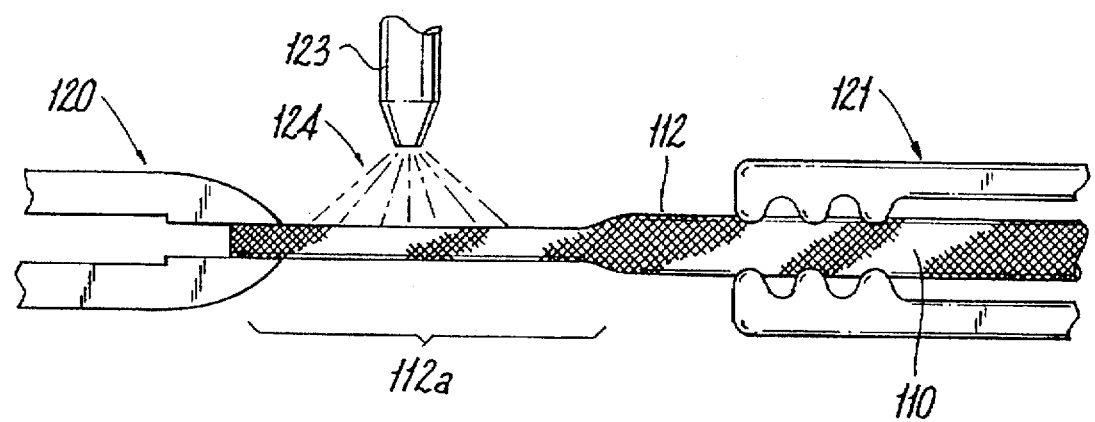

As can be seen in FIG. 4, a portion 112a of sheath 112 has a reduced diameter because it no longer surrounds a core. The core 111 terminates within sheath 112 at a position spaced apart from the end of the suture.

The reduced diameter portion 112a can be from about 50% to 90% of the original diameter of the suture, depending on the proportion of core and sheath strands. By way of example, a suture having a diameter of 0.0205 inches was reduced to about 0.0155 inches in the core-removed end portion. This end portion was inserted into a 0.02 inch outer diameter surgical incision member.

Referring again to FIG. 4, the reduced diameter end portion 112a is preferably tipped with a tipping agent while under tension to maintain the reduced diameter when the tension is released. As seen in FIG. 4, a tipping agent is applied as a mist 124 sprayed from nozzle 123. The preferred tipping agent is cyanoacrylate monomer, which hardens very quickly after it is absorbed into the strands stiffens the suture, of the sheath 112, thereby causing the filaments of the suture to adhere. This adhesion of filaments and strands prevents brooming of the suture when cut, and maintains the reduced diameter of the suture after tension is released. A method suitable for application of cyanoacrylate is disclosed in U.S. Pat. No. 5,269,808. Many other tipping agents are known in the art and may optionally be used in the method described herein. Moreover, known methods other than spraying may be used to apply the tipping agent whether it be cyanoacrylate or another type of agent.

Figure 5:
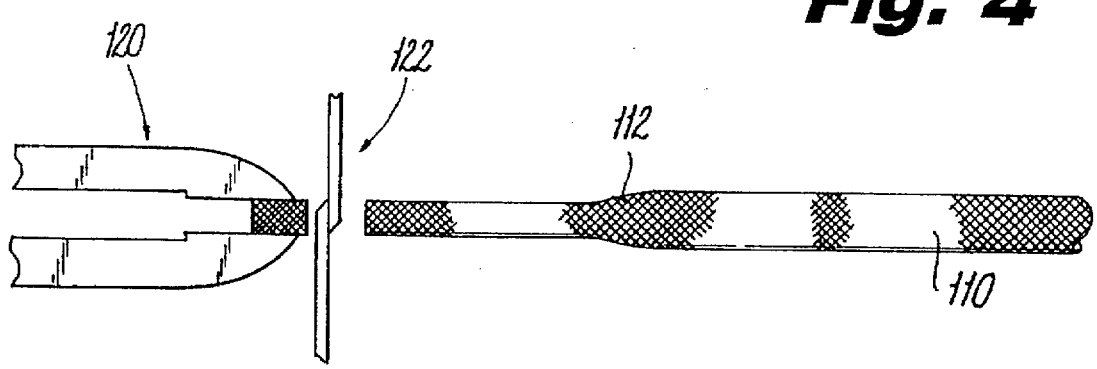

Referring now to FIG. 5, after the tipping agent has been allowed to harden by, for example, drying or curing, cutter 122 may then optionally be used to slice the tip off the reduced diameter portion 112a of the suture to create a cleanly cut tipped end, which may then be inserted into a surgical incision member bore by any of the methods of surgical incision member-suture assembly known in the art. It has been found that a suture prepared in accordance with the present application and attached to a surgical incision member advantageously may meet or exceed USP suture pull out standards for surgical incision member suture combinations.

Figure 6:
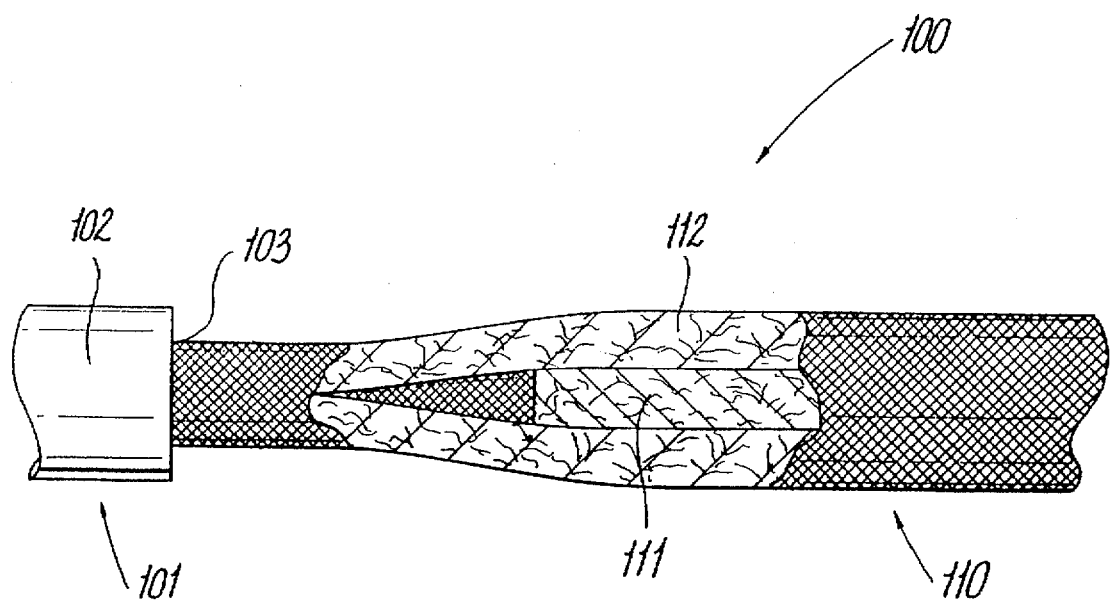
FIG. 6 is a partly sectional elevational view illustrating the connection of a suture modified according to the method described herein to the barrel end of a surgical incision member.

Referring now to FIG. 6, a surgical incision member suture assembly 100 is shown wherein suture 110 having a reduced diameter portion 112a comprising only the braided sheath structure 112, is inserted into bore 103 in the barrel end portion 102 of surgical incision member 101. Use of the present method enables one to join a surgical incision member and suture which both have the same diameter, or even with a surgical incision member somewhat smaller than the suture.

Figure 1:
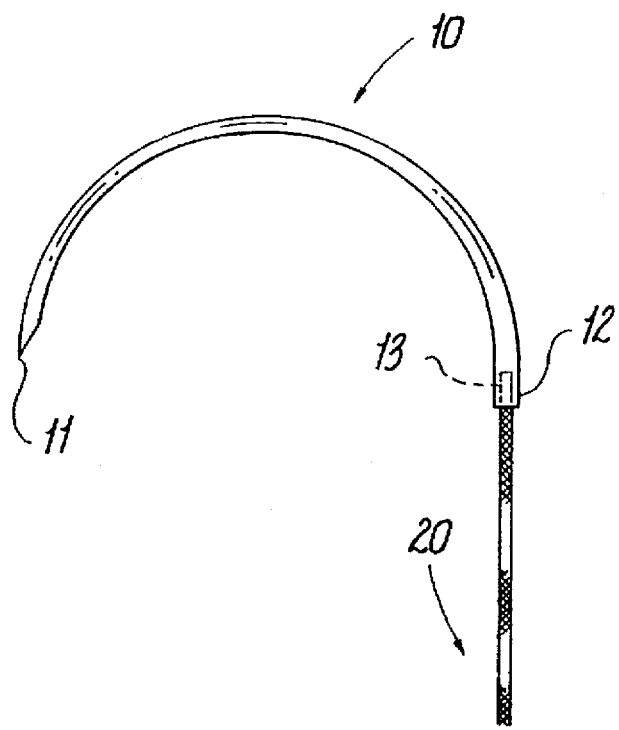
FIG. 1 illustrates a prior art surgical incision member-suture combination.

The surgical incision member suture shown in FIG. 1 is one of several different configurations useful in surgery. Another type of surgical incision member used in surgery is a surgical incision member having a pointed tip at both ends. The surgical incision member typically is shuttled between two opposing jaw members, i.e. alternately released and captured by the jaws as they open and close. The surgical incision member includes a central laterally extending aperture for receiving a suture, which is passed through body tissue as the surgical incision member performs the stitching operation. As the surgical incision member passes through the body tissue it pulls the suture alongside it. Thus, the puncture in the tissue must initially accommodate both the surgical incision member diameter and the suture diameter. The method described herein advantageously reduces the combined surgical incision member-suture diameter by removing the suture core at least in that portion of the suture which lies adjacent the surgical incision member during the operation.

Figure 7:
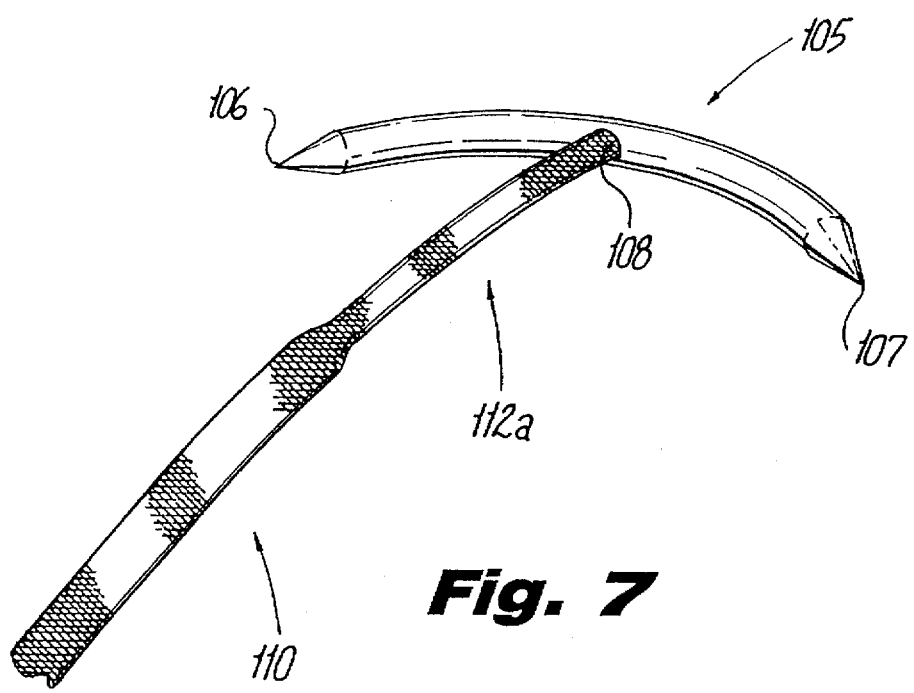
FIG. 7 is an elevational view illustrating a suture modified according to the method described herein attached to a double-tipped surgical incision member.

Referring now to FIG. 7, a combined surgical incision member-suture combination is shown wherein surgical incision member 105 comprises a curved shaft having two opposite pointed ends 105 and 107, and central aperture 108 through which suture 110 is disposed and attached, such as by crimping or gluing. A distal portion 112a of the suture comprises only braided sheath, the core having been removed in accordance with the above method. Surgical incision members are described in co-pending U.S. patent application Ser. No. 08/260,579 filed Jun. 16, 1994. Now U.S. Pat. No. 5,569,301.

In contrast with the surgical incision member-suture embodiment shown in FIG. 6, sutures for use with surgical incision members such as that shown in FIG. 7 either are not tipped or the tipped portion must be removed. Tipping agents stiffen the suture to facilitate insertion into the surgical incision member bore. But sutures used with surgical incision members should easily and flexibly bend at sharp angles as the surgical incision member shuttles back and forth through tissue. Hence, the suture should not be stiffened by a tipped portion. As an alternative, the coreless end portion of the suture may be partially tipped and partially untipped. The tipped portion permits easy insertion though the surgical incision member aperture but it is pulled through the other side of the aperture and completely sliced off leaving a length of untipped coreless sheath portion of sufficient length for use described herein. The suture is preferably secured by crimping the sides of the surgical incision member.

It will be understood that various modifications may be made to the embodiments described herein. Therefore, the above description should not be construed as limiting, but merely as exemplifications of preferred embodiments. Those skilled in the art will envision other modifications within the scope and the spirit of the claims appended hereto.

What is claimed is:

1. A method for attaching a multifilament suture having an interior core and a sheath disposed around the core to a surgical incision member having an aperture for receiving the suture comprising:

a) removing a length of core material from an end portion of the suture to form an end portion of the suture having a sheath without a core; then b) inserting the end portion of the suture having a sheath without a core into the aperture of the surgical incision member; and c) attaching the end portion of the suture having a sheath without a core to the surgical incision member.

2. A method for attaching a multifilament suture having an interior core and a sheath disposed around the core to a surgical incision member having an aperture for receiving the suture comprising:

a) removing a length of core material from an end portion of the suture grasping the sheath, grasping the end of the core, retracting the sheath back to expose a length of core, cutting the core material at a position spaced apart from the end of the core and removing the length of core material, and advancing the sheath to substantially its original configuration to form an end portion of suture having a sheath without a core;

b) inserting the end portion of the suture without a core into the aperture of the surgical incision member; and c) attaching the end portion of the suture without a core to the surgical incision member.

3. The method of claim 2 further comprising the steps of:

applying tension to the coreless end portion of the suture to reduce the diameter of the sheath;

applying a tipping agent to the end portion of the suture; and permitting the tipping agent to harden.

4. The method of claim 3 wherein the tipping agent is cyanoacrylate.

5. The method of claim 3 further comprising the step of cutting the end portion of the sheath.

6. The method of claim 1 wherein suture sheath is braided and the suture core is twisted.

7. The method of claim 1 wherein said suture is bioabsorbable.

8. The method of claim 1 wherein said aperture of said surgical incision member extends axially in a barrel end of the surgical incision member.

9. The method of claim 1 wherein the said surgical incision member has two pointed ends and the aperture extends laterally through the surgical incision member.

10. The method of claim 1 wherein the diameter of the surgical incision member is no larger than the diameter of the cored suture.

11. A surgical incision member-suture combination comprising:

a surgical incision member having a bore to receive a suture end portion;

a multifilament suture having a body portion having a sheath surrounding a suture core and a suture end portion having a sheath only;

the suture end portion being inserted into the bore and the surgical incision member being swaged to the end portion.

* * * * *